(12) United States Patent
Baumfalk et al.

(10) Patent No.: US 8,530,860 B2
(45) Date of Patent: Sep. 10, 2013

(54) OPTICAL SENSOR COMPRISING A LAYER SOLUBLE IN THE MEDIUM TO BE MEASURED AND DEVICE COMPRISING IT, AND PROCESS FOR THEIR PRODUCTION

(75) Inventors: Reinhard Baumfalk, Goettingen (DE); Gerhard Greller, Goettingen (DE); Daniel Riechers, Hannover (DE); Julia Lueders, Lahstedt (DE)

(73) Assignee: Sartorius Stedim Biotech GmbH (DE)

( * ) Notice: Subject to any disclaimer, the term of this patent is extended or adjusted under 35 U.S.C. 154(b) by 24 days.

(21) Appl. No.: 13/389,151

(22) PCT Filed: Jul. 10, 2010

(86) PCT No.: PCT/EP2010/004221
§ 371 (c)(1),
(2), (4) Date: Feb. 16, 2012

(87) PCT Pub. No.: WO2011/015270
PCT Pub. Date: Feb. 10, 2011

(65) Prior Publication Data
US 2012/0132813 A1    May 31, 2012

(30) Foreign Application Priority Data
Aug. 5, 2009   (DE) .......................... 10 2009 036 217

(51) Int. Cl.
*G01N 21/64* (2006.01)
(52) U.S. Cl.
USPC ...................................... 250/459.1
(58) Field of Classification Search
USPC .............................. 250/361 R, 459.1, 458.1
See application file for complete search history.

(56) References Cited

U.S. PATENT DOCUMENTS

| | | | |
|---|---|---|---|
| 6,023,371 A * | 2/2000 | Onitsuka et al. | 359/620 |
| 6,653,148 B2 | 11/2003 | Trapp et al. | |
| 7,390,462 B2 | 6/2008 | Rao et al. | |
| 2002/0106810 A1 | 8/2002 | Singaram et al. | |
| 2011/0035160 A1* | 2/2011 | Rhee et al. | 702/22 |
| 2011/0266449 A1 | 11/2011 | Wuenn et al. | |

FOREIGN PATENT DOCUMENTS

| | | |
|---|---|---|
| DE | 100 51 220 | 4/2002 |
| DE | 10 2009 003 971 | 7/2010 |
| EP | 0 340 018 | 11/1989 |
| EP | 1 795 891 | 6/2007 |
| WO | 02/056023 | 7/2002 |
| WO | 2005/032330 | 4/2005 |

OTHER PUBLICATIONS

International Preliminary Report on Patentability, Mar. 8, 2012.

* cited by examiner

*Primary Examiner* — Kiho Kim
(74) *Attorney, Agent, or Firm* — Gerald E. Hespos; Michael J. Porco; Matthew T. Hespos

(57) ABSTRACT

An optical is provided with reduced sensitivity to radiation, more particularly gamma radiation. The optical sensor is suitable for determining at least one parameter in a medium and includes a matrix containing a fluorescent dye. The matrix is supported by a transparent support. On the side facing the medium, the matrix has a layer soluble in the medium, which layer provides protection against radiation or damaging radiation products. The optical sensor is suitable for implementation in containers and laboratory products, such as disposable bioreactors for example, which are sterilized using gamma radiation.

38 Claims, 1 Drawing Sheet

OPTICAL SENSOR COMPRISING A LAYER SOLUBLE IN THE MEDIUM TO BE MEASURED AND DEVICE COMPRISING IT, AND PROCESS FOR THEIR PRODUCTION

BACKGROUND OF THE INVENTION

1. Field of the Invention

The invention relates to an optical sensor sterilizable by irradiation, for determining at least one parameter in a medium, a device comprising such an optical sensor, and a process for producing the sensor and the device. Optical sensors are used particularly in disposable reactors or containers, mixing reactors or containers, and bioreactors or biocontainers in medical technology and biotechnology. In these and similar application areas, it is often necessary to sterilize a container before use. In the field of disposable products, radiation, more particularly gamma radiation, has been found to be effective for sterilization, but is, however, damaging to optical sensors. This is particularly the case for optical sensors based on porous matrices, such as fluorescence-based pH sensors for example. Therefore, such sensors require an effective protective system which, at the same time, can be implemented cost-effectively.

2. Description of the Related Art

WO 02/056023 A1 and DE 10,051,220 A1 disclose optical sensors for measuring at least one parameter in a sample. These sensors are based on a device for exciting the fluorescence of an analyte-sensitive fluorescent dye immobilized in a matrix in a sample vessel or reactor, which dye is in at least indirect contact with the sample, and on an evaluation device for the resulting fluorescence response signal. The analyte concentration can be evaluated or determined in this case by utilizing both the fluorescence decay time and the fluorescence intensity. A disadvantage is that such pH sensor patches, based on a hydrophilic support matrix, such as, for example, impregnated papers or sol-gel matrices, are damaged in a dose-dependent manner during radiation sterilization. There is a reduction in both the intensity of the fluorescence of the dye(s), and the sensitivity of the sensor patch with respect to the measured variable.

U.S. Pat. No. 7,390,462 B2 discloses a sensor in which the fluorescent dye is present immobilized in a hydrophilic matrix. It claims a sensor having the pH-sensitive fluorescent dye MA-HPDS present in a hydrogel. In this case, too, it is a disadvantage that such hydrophilic optical sensors are damaged in a dose-dependent manner during sterilization with gamma radiation. Such radiation is used particularly in laboratory technology for containers composed of polymers. There is a reduction in both the intensity of the fluorescence of the dye(s) and the sensitivity of the sensor with respect to the measured variable. Particularly severe damage to such a sensor patch occurs when it is in contact during the radiation sterilization with a relatively large volume of air, or else with conventional protective gasses such as, for example, nitrogen or argon. During the radiation sterilization, the gasses are partly ionized, or free radicals are generated. These radicals react, for example, during the sterilization of a gas-filled polymer bag, on the wells or else on the sensor surfaces. Sensors based on porous, hydrophilic matrices are particularly vulnerable to this, since the sensor chemistry as a matter of principle has to be present immobilized on the surface, or inner surface, of the matrix, so that the sample to be measured can come into contact with the sensor chemistry. The extent of the damage depends firstly on the irradiation dose and secondly on the ratio of surface area to volume of the irradiated container containing the sensor patch. This ratio determines the number of ions or radicals which damage the sensor patch, or the sensor chemistry contained therein.

DE 10 2009 003 971.6 A1 discloses an optical sensor for measuring at least one parameter, which sensor is porously covered by a noble metal layer, and so reaction of reactive ions on the noble metal layer is achieved. However, a disadvantage in this case is that such a coating is technically and mechanically difficult to achieve and is associated with high costs, and this should be avoided particularly in the field of disposable products.

It is therefore an object of the present invention, firstly, to develop an optical sensor and a device comprising it in which the sensitivity of the optical sensor to radiation, more particularly gamma radiation, is reduced and which is implementable in a cost-effective and simple manner, and, secondly, to specify a process for their production.

SUMMARY OF THE INVENTION

The optical sensor according to the invention measures one or more parameters in a medium. The optical sensor essentially comprises three layers superimposed on top of one another. A transparent support which is penetratable by excitation light serves as base layer. On this support sits a matrix containing at least one fluorescent dye. To protect the latter layer, it is covered by a soluble layer. The soluble layer dissolves in an added aqueous medium only through contact therewith. The sensitivity to reactive particles produced during gamma irradiation is greatly reduced. This results in a better signal-to-noise ratio, and a generally higher sensitivity of the optical sensor with respect to its measured variable. At the same time, certain processes in a cell culture medium or fermentation medium, for example, can be induced or inhibited by the dissolved substance. The soluble layer can additionally have a safety function and stabilization function with respect to the sensor chemistry located therebelow in the form of the matrix containing the at least one fluorescent dye, for example during transportation.

According to a preferred embodiment of the invention, the optical sensor is sterilizable by radiation while maintaining its functionality. The soluble layer greatly reduces the sensitivity to sterilization, for example by means of ionizing radiation, gamma radiation, UVC, beta or electron radiation. In the gas phase surrounding the optical sensor, the reactive particles formed as a result of the radiation no longer react with the matrix and with the fluorescent dye(s) itself/themselves. Thus, a better signal-to-noise ratio, and a generally higher sensitivity of the optical sensor with respect to its measured variable, is achieved. The measured variables can in this case be, for example, pH, the dissolved oxygen concentration or other parameters.

According to a further preferred embodiment of the invention, the matrix of the optical sensor is hydrophilic. Particular embodiments may be a sol-gel matrix or a hydrogel in which the fluorescent dye is present in immobilized form. The hydrophilic character is particularly necessary for optical sensors whose matrix-embedded fluorescent dye has to be accessible to an aqueous medium. Optical sensors comprising a hydrophilic matrix are by nature extremely sensitive to sterilization, for example by means of gamma radiation. The soluble layer provides effective protection against these influences.

According to a further particularly preferred embodiment of the invention, the matrix of the optical sensor is porous.

According to a further preferred embodiment, the medium to be measured can also partially penetrate the soluble layer of the optical sensor. The soluble layer does not have to be dissolved in its entirety, since penetration thereof, and thus contacting of the matrix by the medium, is possible. A soluble layer partly containing insoluble substances can thus lie over the matrix as an additional porous protective matrix.

According to a particularly preferred embodiment of the invention, the layer, soluble in the medium to be measured, of the optical sensor has a thickness of 10 nm to 2 mm.

According to a particularly preferred embodiment of the invention, the soluble layer is composed of one or more sugars, inorganic salts, amino acids, glycerol, polyvinyl alcohols, peptides, proteins or a combination thereof. It has been found to be particularly advantageous in this case for the soluble layer to have a residual moisture content of 5-10%. In this way, secure protection during sterilization and simple dissolution of the soluble layer is achievable.

In a further advantageous embodiment of the invention, the soluble layer opposing the medium to be measured is inert with respect to the optical sensor. This ensures trouble-free, correct performance of the optical sensor.

In an advantageous embodiment of the invention, the layer soluble in the medium to be measured is inert with respect to the medium to be measured itself. The layer dissolves owing to said medium, but does not result in any further products.

According to a further preferred embodiment, the layer soluble in the medium to be measured is metabolizable by microorganisms or cell cultures. Thus, introduction of undesired substances, or a surplus of substances to be metabolized, is preventable prior to processes by an appropriate calculation. It is also possible to utilize a reverse effect, by dissolved substances acting as inhibitors of certain processes.

In a further preferred embodiment of the invention, the object is additionally achieved by a device for accommodating a medium. The device for accommodating a medium comprises an optical sensor. The latter measures one or more parameters in a medium. The optical sensor essentially comprises three layers superimposed on top of one another. A transparent support which can be penetrated by excitation light serves as base layer. On this support sits a matrix containing at least one fluorescent dye. To protect the latter layer, it is covered by a soluble layer. The soluble layer dissolves in an added medium only through contact therewith. The sensitivity to reactive particles produced during gamma irradiation is greatly reduced. This results in a better signal-to-noise ratio, and a generally higher sensitivity of the sensor element with respect to its measured variable. At the same time, certain processes in a cell culture medium or fermentation medium, for example, can be induced or inhibited by the dissolved substance. The soluble layer can additionally have a safety function and stabilization function with respect to the sensor chemistry located therebelow in the form of the matrix containing the at least one fluorescent dye, for example during transportation.

According to a preferred embodiment of the invention, the device is sterilizable by radiation while maintaining its functionality. The soluble layer greatly reduces the sensitivity of the optical sensor to sterilization, for example by means of ionizing radiation, gamma radiation, UVC, beta or electron radiation. In the gas phase surrounding the optical sensor, the reactive particles formed as a result of the radiation no longer react with the matrix and with the fluorescent dye(s) itself/themselves. Thus, a better signal-to-noise ratio, and a generally higher sensitivity of the optical sensor with respect to its measured variable, is achieved. The measured variables can in this case be, for example, pH, dissolved oxygen concentration or other parameters.

According to a further preferred embodiment of the invention, the matrix of the optical sensor of the device is hydrophilic. Particular embodiments may be a sol-gel matrix or a hydrogel in which the fluorescent dye is present in immobilized form. The hydrophilic character is particularly necessary for optical sensors, whose matrix-embedded fluorescent dye has to be accessible to an aqueous medium. Optical sensors comprising a hydrophilic matrix are by nature extremely sensitive to sterilization, for example by means of gamma radiation. The soluble layer provides effective protection against these influences.

According to a further particularly preferred embodiment of the invention, the matrix of the optical sensor of the device is porous.

According to a further preferred embodiment, the medium to be measured can also partially penetrate the soluble layer of the optical sensor of the device. The soluble layer does not have to be dissolved in its entirety, since penetration thereof, and thus contacting of the matrix by the medium, is possible. A soluble layer partly bearing insoluble substances can thus lie over the matrix as an additional porous protective matrix.

According to a particularly preferred embodiment of the invention, the layer soluble in the medium to be measured, of the optical sensor of the device has a thickness of 10 nm to 2 mm.

According to a particularly preferred embodiment of the invention, the soluble layer of the optical sensor of the device is composed of one or more sugars, inorganic salts, amino acids, glycerol, polyvinyl alcohols, peptides, proteins or a combination thereof. It has been found to be particularly advantageous in this case for the soluble layer to have a residual moisture content of 5-10%. In this way, simple dissolution of the soluble layer is ensured.

In a further advantageous embodiment of the invention, the layer soluble in the medium to be measured, of the optical sensor of the device is inert with respect to the optical sensor, and this ensures trouble-free, correct performance of the optical sensor.

In an advantageous embodiment of the invention, the layer soluble in the medium to be measured, of the optical sensor of the device is inert with respect to the medium to be measured itself. The layer dissolves owing to said medium, but does not result in any further products.

According to a further preferred embodiment, the layer soluble in the medium to be measured, of the optical sensor of the device is metabolizable by microorganisms or cell cultures. Thus, introduction of additional substances, or a surplus of substances to be metabolized, is preventable prior to processes by an appropriate calculation. It is also possible to utilize a reverse effect, by dissolved substances acting as inhibitors of certain processes.

According to a particularly preferred embodiment of the device according to the invention, said device comprises a sender and/or receiver for wireless communication. This can, for example, be effected by means of known technologies such as Bluetooth or RFID.

The invention further relates to a process. In the process according to the invention, essentially two steps are used in the production of an optical sensor. Firstly, the application of a matrix comprising at least one fluorescent dye onto a transparent support layer and, secondly, the application of a water-soluble layer onto the matrix. The soluble layer can in this case be, for example, an aqueous solution containing one or more sugars, inorganic salts, amino acids, peptides, proteins, glycerol, polyvinyl alcohols.

In a further preferred process for producing a device comprising an optical sensor for determining at least one parameter in a medium, in which device the functionality of the optical sensor is maintained after sterilization by irradiation, essentially the following process steps are used: firstly, the optical sensor is combined with the device for accommodating the medium; subsequently, the device is irradiated by means of radiation.

In a preferred process according to the invention, the device is irradiated using ionizing radiation, for example by means of gamma radiation, UVC, beta or electron radiation.

In a further particularly preferred process, a container composed of plastic and having at least partially flexible walls is used for the device. Such containers are cost-effective to produce. In the case of disposable products, there is additionally no need for time-consuming and costly cleaning. One or more optical sensors may be implemented in a container composed of plastic. Despite necessary sterilization of the plastic container using radiation, sensor measurement performance is maintained.

The invention will be explained in more detail by means of the exemplary embodiment below.

Example

The sensor chemistry of three pH sensors (HP8, Presens GmbH, Regensburg) on a polycarbonate cap is impregnated with 10 µl of glycerol (99%, Sigma-Aldrich, Schnelldorf); 3 further sensors of the same type are treated in the same way with 10 µl of a 50% strength glucose solution (glucose monohydrate, Sigma-Aldrich, Schnelldorf). The six treated sensors are dried at 40° C. overnight in a drying cabinet together with three untreated sensors of the same type. The altogether nine sensors are introduced into a plastic container (Cultibag RM, Sartorius Stedim Biotech GmbH, Göttingen/volume: 10 l) and attached in such a way that the sensor chemistry faces the center of the container. The device is packed in a black, lightproof PE bag. Subsequently, gamma irradiation is carried out at 28.0 kGy (Co-60 source, Beta-Gamma-Service GmbH & Co. K G, Wiehl). After irradiation, the sensors are removed from the container and measured using a transmitter (pH-1 mini, Presens GmbH, Regensburg) in buffers having pH values of 6.0 and 8.0. The sensitivity and thus the quality of the sensors corresponds to the difference between the phases at pH 6.0 and pH 8.0. Corresponding values are reported in the following table.

| Sensor, pretreated with | Gamma dose [kGy] | Δ Phase [°] (average from 3 sensors in each case) |
|---|---|---|
| Untreated | 28.0 | 19 |
| 10 µl Glycerol | 28.0 | 20 |
| 10 µl Glucose solution, 50% | 28.0 | 23 |

As is evident from the above table, the sensitivity of the impregnated sensors is greater than that of the untreated sensors.

DETAILED DESCRIPTION OF THE PREFERRED EMBODIMENT

Figure 1:
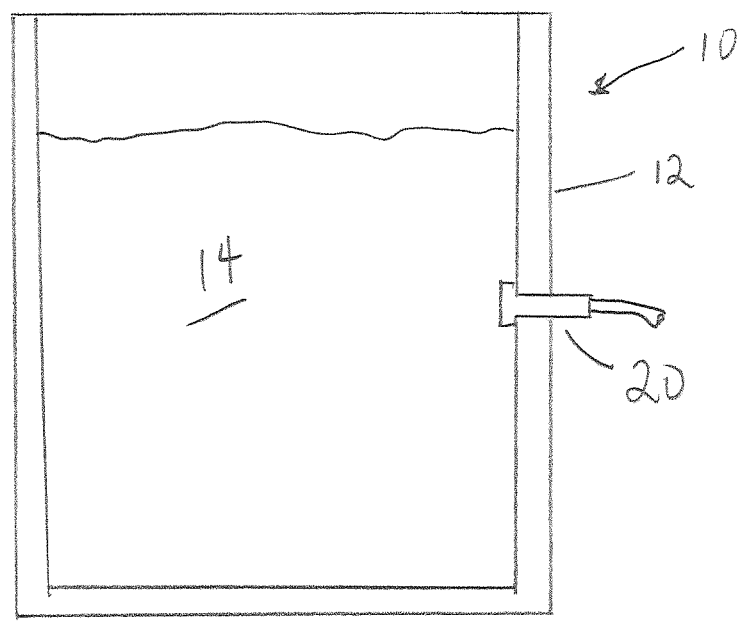
FIG. 1 is a schematic illustration of a device in accordance with the invention.
Figure 2:
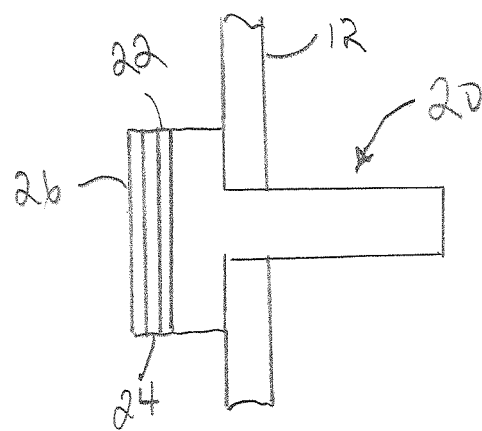
FIG. 2 is a schematic illustration of the optical sensor of the device shown in FIG. 1.

A device in accordance with the invention is identified generally by the numeral 10 in FIG. 1. The device 10 is in the form of a container made of plastic and has at least one flexible wall 12. The device 10 is configured for storing a liquid medium 14. An optical sensor 20 is mounted to the wall 12 for determining at least one parameter of the medium 14 in the device 10. The device 10 may require sterilization before placing the medium 14 therein. The sterilization preferably is carried out by exposing at least the interior of the device 10 to radiation prior to placing the medium 14 in the device 10. The radiation used in sterilization has the potential of damaging the optical sensor 20. Accordingly, the surface of the optical sensor 20 that will be within the device and exposed to both the radiation and the liquid medium 14 has three layers superimposed thereon. More particularly, a transparent support layer 22 that can be penetrated by excitation light is applied initially to the optical sensor 20. A matrix 24 containing at least one fluorescent dye is applied on the transparent support layer 22. To protect the matrix 24, a soluble layer 26 is applied over the matrix 24. The soluble layer 26 is formed from a material that dissolves in an aqueous medium through contact therewith. The soluble layer 26 greatly reduces the sensitivity to sterilization by ionizing radiation, gamma radiation, UVC, based on or electron radiation.

The invention claimed is:

1. An optical sensor for determining at least one parameter in a medium, which sensor comprises at least one matrix which contains at least one fluorescent dye, is supported by a transparent support, and has on the side facing the medium a layer soluble in the medium to be measured.

2. The optical sensor of claim 1, which is sterilizable by radiation while maintaining its functionality.

3. The optical sensor of claim 2, wherein the radiation is ionizing radiation.

4. The optical sensor of claim 2, wherein the radiation is gamma radiation.

5. The optical sensor of claim 2, wherein the radiation is electron radiation.

6. The optical sensor of claim 1, wherein the matrix is hydrophilic.

7. The optical sensor of claim 1, wherein the matrix is porous.

8. The optical sensor of claim 1, wherein the medium to be measured penetrates the soluble layer.

9. The optical sensor of claim 1, wherein the matrix is a sol-gel matrix or a hydrogel.

10. The optical sensor of claim 1, wherein the layer soluble in the medium to be measured has a thickness of 10 nm to 2 mm.

11. The optical sensor of claim 1, wherein the layer soluble in the medium to be measured is composed of one or more sugars, inorganic salts, amino acids, glycerol, polyvinyl alcohols, peptides, proteins or a combination thereof.

12. The optical sensor of claim 1, wherein the residual moisture content of the soluble layer is 5-10%.

13. The optical sensor of claim 1, wherein the layer soluble in the medium to be measured is inert with respect to the optical sensor.

14. The optical sensor of claim 1, wherein the layer soluble in the medium to be measured is inert with respect to the measuring medium.

15. The optical sensor of claim 1, wherein the layer soluble in the medium to be measured is metabolizable by microorganisms or cell cultures.

16. A process for producing the optical sensor of claim 1, comprising the steps of:
applying a matrix comprising at least one fluorescent dye onto a transparent support layer;

applying a layer soluble in the medium to be measured onto the matrix.

17. The process of according to claim 16, wherein the layer soluble in the medium to be measured is applied by applying an aqueous solution containing one or more sugars, inorganic salts, amino acids, glycerol, polyvinyl alcohols, peptides, proteins.

18. A device for accommodating a medium, the device comprising an optical sensor for determining at least one parameter in a medium, wherein the optical sensor comprises at least one matrix which contains at least one fluorescent dye, is supported by a transparent support, and has on the side facing the medium a layer soluble in the medium to be measured.

19. The device of claim 18, which is sterilizable by radiation while maintaining its functionality.

20. The device of claim 19, wherein the radiation is ionizing radiation.

21. The device of claim 19, wherein the radiation is gamma radiation.

22. The device of according to claim 19, wherein the radiation is electron radiation.

23. The device of claim 18, wherein the matrix is hydrophilic.

24. The device of claim 18, wherein the matrix is porous.

25. The device of claim 18, wherein the medium to be measured penetrates the soluble layer.

26. The device of claim 18, wherein the matrix is a sol-gel matrix or a hydrogel.

27. The device of claim 18, wherein the layer soluble in the medium to be measured has a thickness of 10 nm to 20 mm.

28. The device of claim 18, wherein the layer soluble in the medium to be measured is composed of one or more sugars, inorganic salts, amino acids, glycerol, polyvinyl alcohols, peptides, proteins or a combination thereof.

29. The device of claim 18, wherein the residual moisture content of the soluble layer is 5-10%.

30. The device of claim 18, wherein the layer soluble in the medium to be measured is inert with respect to the optical sensor.

31. The device of claim 18, wherein the layer soluble in the medium to be measured is inert with respect to the measuring medium.

32. The device of claim 18, wherein the layer soluble in the medium to be measured is metabolizable by microorganisms or cell cultures.

33. The device of claim 18, comprising a sender and/or receiver for wireless communication.

34. A process for producing the device of claim 18, the device having an optical sensor for determining at least one parameter in a medium, in which device the functionality of the optical sensor is maintained after sterilization by irradiation, the process comprising the steps of:
  combining the optical sensor with the device for accommodating the medium;
  irradiating the device by means of radiation.

35. The process of claim 34, wherein the device is irradiated using ionizing radiation.

36. The process of claim 34, wherein the device is irradiated using gamma radiation.

37. The process of claim 34, wherein the device is irradiated using electron radiation.

38. The process of claim 34, wherein a container composed of plastic and having at least partially flexible walls is used for the device.

* * * * *